United States Patent
Plata-Salaman et al.

(10) Patent No.: US 7,122,576 B2
(45) Date of Patent: Oct. 17, 2006

(54) CARBAMATE COMPOUNDS FOR USE IN PREVENTING OR TREATING BIPOLAR DISORDER

(76) Inventors: Carlos R. Plata-Salaman, 1313 Squire Dr., Ambler, PA (US) 19002; Boyu Zhao, 106 Weymouth Cir., Lansdale, PA (US) 19446; Roy E. Twyman, 3355 Byron Dr., Doylestown, PA (US) 18901; Yong Moon Choi, 2 Van Duyne Ct., Towaco, NJ (US) 07082; Robert Gordon, 2 Hobbs Ct., Robbinsville, NJ (US) 08691

(*) Notice: Subject to any disclaimer, the term of this patent is extended or adjusted under 35 U.S.C. 154(b) by 0 days.

(21) Appl. No.: 10/081,606

(22) Filed: Feb. 21, 2002

(65) Prior Publication Data

US 2002/0193433 A1 Dec. 19, 2002

Related U.S. Application Data

(60) Provisional application No. 60/271,680, filed on Feb. 27, 2001.

(51) Int. Cl.
*A01N 47/10* (2006.01)
*A61K 31/27* (2006.01)

(52) U.S. Cl. .................................................. 514/483
(58) Field of Classification Search ................ 514/483
See application file for complete search history.

(56) References Cited

U.S. PATENT DOCUMENTS

| | | | |
|---|---|---|---|
| 3,265,728 A | | 8/1966 | Bossinger et al. |
| 3,278,380 A | | 10/1966 | Bossinger et al. |
| 3,313,692 A | | 4/1967 | Bossinger et al. |
| 5,698,588 A | * | 12/1997 | Choi et al. .................. 514/483 |
| 5,854,283 A | * | 12/1998 | Choi et al. .................. 514/483 |
| 6,103,759 A | * | 8/2000 | Choi et al. .................. 514/489 |
| 6,127,412 A | * | 10/2000 | Choi et al. .................. 514/483 |

OTHER PUBLICATIONS

U.S. Appl. No. 09/906,251, Ortho-McNeil Pharmaceutical, Inc.
U.S. Appl. No. 10/081,764, Ortho-McNeil Pharmaceutical, Inc.
U.S. Appl. No. 10/081,501, Ortho-McNeil Pharmaceutical, Inc.
U.S. Appl. No. 10/081,943, Ortho-McNeil Phamaceutical, Inc.
U.S. Appl. No. 10/081,766, Ortho-McNeil Pharmaceutical, Inc.
U.S. Appl. No. 10/081,761, Ortho-McNeil Pharmaceutical, Inc.
U.S. Appl. No. 10/081,713, Ortho-McNeil Pharmaceutical, Inc.
U.S. Appl. No. 10/193,600, Ortho-McNeil Pharmaceutical, Inc.
U.S. Appl. No. 10/192,973, Ortho-McNeil Pharmaceutical, Inc.
International PCT Search Report PCT/US02/05541 dated Jul. 8, 2002.

Akisakl, H.S., et al., *Re-evaluatiang the Prevalence of and Diagnostic Composition Within the Broad Clinical Spectrum of Bipolar Disorders*, J. Affect. Disord., 2000, 59 (*Suppl 1), S5-S30.
Goodwin, F., et al., *Manic-Depressive Illness*, Oxford University Press, New York, 1990, pp 405-407.
Ghaemi, S.N., et al., *Kindling and Second Messengers: An Approach to the Neurobiology of Recurrence in Bipolar Disorder*, Biol. Psychiatry, 1999, 45(2) 137-144.
Stoll, A.L., et al., *Mood Stabilizers: Shared Mechanisms of Action at Postsynaptic Signal-Transduction and Kindling Processes*, Harv. Rev. Psychiatry, 1996, 4(2), 77-89.
Janowsky, D.S. *New Treatments of Bipolar Disorder*, Curr. Psychiatry Rep., 1999 1(2), 111-113.
Shelton, M.D., et al., *Current Concepts in Rapid Cycling Bipolar Disorder*, Curr. Psychiatry Rep., 2000, 2(4), 310-315.
Lennkh, C., et al., *Current Aspects of Valproate in Bipolar Disorder*, Int. Clin. Psychopharmacol., 2000, 15(1), 1-11.
Tohen, M., et al., *Management of Acute Mania*, J. Clin. Psuchiatry, 1999, 60, (Suppl 5) 31-34.
Muller-Oerlinghausen, B., et al., *Valproate as an Adjunct to Neuroleptic Medication for the Treatment of Acute Episodes of Mania: A Prospective, Randomized, Double-Blind, Placebo-Controlled, Multicenter Study*, European Valproate Mania Study Group, J. Clin. Psychopharmacol., 2000 20(2), 195-203.

(Continued)

*Primary Examiner*—Christopher S. F. Low
*Assistant Examiner*—Amy A. Lewis

(57) ABSTRACT

This invention is directed to a method for preventing or treating bipolar disorder comprising administering to a subject in need thereof a therapeutically effective amount of an enantiomer of Formula (I) or enantiomeric mixture wherein one enantiomer of Formula (I) predominates:

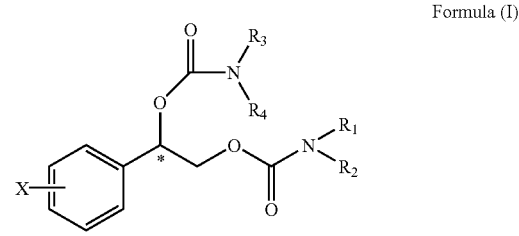

Formula (I)

wherein phenyl is substituted at X with one to five halogen atoms selected from the group consisting of fluorine, chlorine, bromine and iodine; and, $R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

17 Claims, No Drawings

OTHER PUBLICATIONS

Sachs, G.S., et al., *The Expert Consensus Guideline Series, Medication Treatment of Bipolar Disorder 2000,* Postgrad. Med., 2000, Spec No: 1-104.

*Bipolar Disorder,* Cognos Study #53, Decision Resources, Mar. 2000.

Wauquier, A., et al., *Topiramate: A Potent Anticonvulsant in the Amygdala-Kindled Rat,* Epilepsy Res., 1996, 24, 73-77.

Goldberg, J.F., et al., *Kindling in Bipolar Disorders: A Longitudinal Follow-up Study,* Biol. Psychiatry, 1994, 1; 35(1), 70-72.

Sadock, B.J., et al., *Treatment of Bipolar Disorders,* Comprehensive Textbook of Psychiatry, 2000, vol. 1, 1385-1430.

Post, R.M., et al., *A History of the Use of Anticonvulsants as Mood Stabilizers in the Last Two Decades of the 20$^{th}$ Century,* Neuropsychobiology, Abstract, 1998, 38(3), 152-166.

Diagnostic and Statistical Manual of Mental Disorders, Edition 4, American Psychiatric Association, Washington, D.C., 1994.

Lothman et al, "Screening and Characterization of Antiepileptic Drugs with Rapidly Recurring Hippocampal Seizures in Rats", *Epilepsy Res.,* vol. 2, No. 6, pp 367-379 (Nov.-Dec. 1988).

Morozova MA, "The new approaches to treatment of depression at bipolar affective disorders," 2001 Psikhiatriya I Psikhofarmakologiya 3(1): 1-8; translation from Russian.*

Post et al., "A History of the Use of Anticonvulsants as Mood Stabilizers in the Last Two Decades of the 20$^{th}$ Century", Neuropsychobiology (1988), vol. 38, pp. 152-166.

* cited by examiner

CARBAMATE COMPOUNDS FOR USE IN PREVENTING OR TREATING BIPOLAR DISORDER

CROSS REFERENCE TO RELATED APPLICATIONS

This application claims benefit of provisional application Ser. No. 60/271,680, filed Feb. 27, 2001, which is hereby incorporated by reference.

FIELD OF THE INVENTION

This invention is directed to a method for use of a carbamate compound in preventing or treating bipolar disorder. More particularly, this invention is directed to a method for use of a halogenated 2-phenyl-1,2-ethanediol dicarbamate enantiomer or enantiomeric mixture wherein one enantiomer predominates for preventing or treating bipolar disorder.

BACKGROUND OF THE INVENTION

Bipolar disorder is a progressive psychiatric disorder (F. Goodwin and K. R. Jamison, Manic-Depressive Illness, Oxford University Press, New York, 1990). Bipolar disorder is characterized by recurrent episodes of changes in mood. The episodes may exhibit symptoms of mania, hypomania (less severe form of mania), depression, or a combination of mania and depression (Bipolar Disorder, Cognos Study #53, Decision Resources, March 2000). Bipolar disorder type I features more manic or mixed mood symptoms, while bipolar disorder type II is distinguished by primarily depressive episodes but also by spontaneous hypomanic episodes (Diagnostic and Statistical Manual of Mental Disorders, Edition 4, American Psychiatric Association, Washington D.C., 1994; Bipolar Disorder, Cognos Study #53, Decision Resources, March 2000; Akiskal H. S., Bourgeois M. L., Angst J., Post R., Moller H., Hirschfeld R., Re-evaluating the prevalence of and diagnostic composition within the broad clinical spectrum of bipolar disorders, *J. Affect. Disord.,* 2000, 59 (Suppl 1), S5–S30). Acute mania is associated with an elevated or irritable mood and at least three to four classical mania signs and symptoms (e.g., abnormally elevated or irritable mood, grandiosity or inflated self-esteem, decreased sleep, racing thoughts, distractibility) (Diagnostic and Statistical Manual of Mental Disorders, Edition 4, American Psychiatric Association, Washington D.C., 1994). Hypomania is associated with a period of mild mood elevation, sharpened positive thinking and increased energy and activity levels, but without the impairment associated with maniac episodes (Diagnostic and Statistical Manual of Mental Disorders, Edition 4, American Psychiatric Association, Washington D.C., 1994). Rapid cycling is defined as alternation of depression and mania/excitation (Akiskal H. S., Bourgeois M. L., Angst J., Post R., Moller H., Hirschfeld R., Re-evaluating the prevalence of and diagnostic composition within the broad clinical spectrum of bipolar disorders, *J. Affect. Disord.,* 2000, 59 (Suppl 1), S5–S30). Cyclothymic disorder is an attenuated bipolar disorder characterized by frequent short cycles of subsyndromal depression and hypomanic episodes (Diagnostic and Statistical Manual of Mental Disorders, Edition 4, American Psychiatric Association, Washington D.C., 1994).

Recurrences of bipolar disorder illness have been hypothesized to be caused by electrophysiologic/neurophysiologic kindling (F. Goodwin and K. R. Jamison, Manic-Depressive Illness, Oxford University Press, New York, pp 405–407, 1990; Ghaemi S. N., Boiman E. E., Goodwin F. K., Kindling and second messengers: an approach to the neurobiology of recurrence in bipolar disorder, *Biol. Psychiatry,* 1999, 45(2), 137–44; Stoll A. L., Severus W. E., Mood stabilizers: shared mechanisms of action at postsynaptic signal-transduction and kindling processes, *Harv. Rev. Psychiatry,* 1996, 4(2), 77–89; Goldberg J. F., Harrow M., Kindling in bipolar disorders: a longitudinal follow-up study, *Biol. Psychiatry,* 1994, 1; 35(1), 70–2).

Mood stabilizers are used to treat bipolar disorder (Sadock B. J., Sadock B. A., Post RM. Treatment of bipolar disorders, *Comprehensive Textbook of Psychiatry,* 2000, vol. 1, 1385–1430). Established mood stabilizers exhibit anti-kindling effects (Stoll A. L., Severus W. E., Mood stabilizers: shared mechanisms of action at postsynaptic signal-transduction and kindling processes, *Harv. Rev. Psychiatry,* 1996, 4(2), 77–89). Anticonvulsants and anti-epileptics which show anti-kindling effects are important alternatives and adjuncts in the treatment of bipolar illness (Post R. M., Denicoff K. D., Frye M. A., Dunn R. T., Leverich G. S., Osuch E., Speer A., A history of the use of anticonvulsants as mood stabilizers in the last two decades of the 20th century, *Neuropsychobiology,* 1998, 38(3), 152–66; Janowsky D. S., New Treatments of Bipolar Disorder, *Curr. Psychiatry Rep.,* 1999, 1(2), 111–113) including in rapid cycling bipolar disorder (Shelton M. D., Calabrese J. R., Current Concepts in Rapid Cycling Bipolar Disorder, *Curr. Psychiatry Rep.,* 2000, 2(4), 310–315) and in the treatment and prevention of acute mania (Lennkh C., Simhandl C., Current aspects of valproate in bipolar disorder, *Int. Clin. Psychopharmacol,* 2000, 15(1), 1–11; Tohen M., Grundy S., Management of acute mania, *J. Clin. Psychiatry,* 1999, 60 (Suppl 5) 31–4; Muller-Oerlinghausen B., Retzow A., Henn F. A., Giedke H., Walden J., Valproate as an adjunct to neuroleptic medication for the treatment of acute episodes of mania: a prospective, randomized, double-blind, placebo-controlled, multicenter study, European Valproate Mania Study Group, *J. Clin. Psychopharmacol.,* 2000, 20(2), 195–203; Sachs G. S., Printz D. J., Kahn D. A., Carpenter D., Docherty J. P., The Expert Consensus Guideline Series: Medication Treatment of Bipolar Disorder 2000. *Postgrad. Med.,* 2000, Spec No: 1–104).

Substituted phenyl alkyl carbamate compounds have been described in U.S. Pat. No. 3,265,728 to Bossinger, et al (hereby incorporated by reference), as useful in treating the central nervous system, having tranquilization, sedation and muscle relaxation properties of the formula:

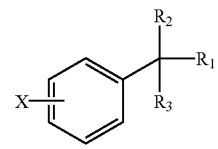

wherein $R_1$ is either carbamate or alkyl carbamate containing from 1 to 3 carbon atoms in the alkyl group; $R_2$ is either hydrogen, hydroxy, alkyl or hydroxy alkyl containing from 1 to 2 carbons; $R_3$ is either hydrogen or alkyl containing from 1 to 2 carbons; and X can be halogen, methyl, methoxy, phenyl, nitro or amino.

A method for inducing calming and muscle relaxation with carbamates has been described in U.S. Pat. No. 3,313, 692 to Bossinger, et al (hereby incorporated by reference) by administering a compound of the formula:

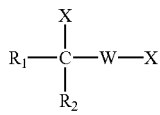

in which W represents an aliphatic radical containing less than 4 carbon atoms, wherein $R_1$ represents an aromatic radical, $R_2$ represents hydrogen or an alkyl radical containing less than 4 carbon atoms, and X represents hydrogen or hydroxy or alkoxy and alkyl radicals containing less than 4 carbon atoms or the radical:

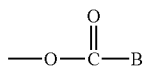

in which B represents an organic amine radical of the group consisting of heterocyclic, ureido and hydrazino radicals and the radical —$N(R_3)_2$ wherein $R_3$ represents hydrogen or an alkyl radical containing less than 4 carbon atoms.

Optically pure forms of halogen substituted 2-phenyl-1, 2-ethanediol monocarbamates and dicarbamates have also been described in U.S. Pat. No. 6,103,759 to Choi, et al (hereby incorporated by reference), as effective for treating and preventing central nervous system disorders including convulsions, epilepsy, stroke and muscle spasm; and as useful in the treatment of central nervous system diseases, particularly as anticonvulsants, antiepileptics, neuroprotective agents and centrally acting muscle relaxants, of the formulae:

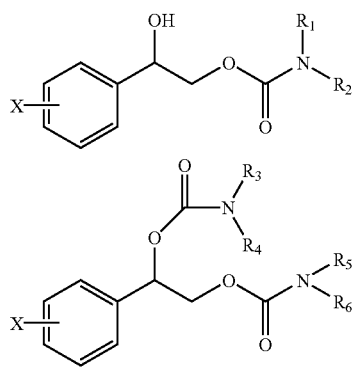

wherein one enantiomer predominates and wherein the phenyl ring is substituted at X with one to five halogen atoms selected from fluorine, chlorine, bromine or iodine atoms and $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. Pure enantiomeric forms and enantiomeric mixtures were described wherein one of the enantiomers predominates in the mixture for the compounds represented by the formulae above; preferably one of the enantiomers predominates to the extent of about 90% or greater; and, most preferably, about 98% or greater.

A halogen substituted 2-phenyl-1,2-ethanediol dicarbamate enantiomer of Formula (I) or enantiomeric mixture wherein one enantiomer of Formula (I) predominates has not been previously described as useful for preventing or treating bipolar disorder. Recent preclinical studies have revealed previously unrecognized pharmacological properties which suggest that an enantiomer of Formula (I) or enantiomeric mixture wherein one enantiomer of Formula (I) predominates is useful in preventing or treating bipolar disorder. Therefore, it is an object of the present invention to teach a method for use of an enantiomer of Formula (I) or enantiomeric mixture wherein one enantiomer of Formula (I) predominates in preventing or treating bipolar disorder.

SUMMARY OF THE INVENTION

The present invention is directed to a method for preventing or treating bipolar disorder comprising administering to a subject in need thereof a therapeutically effective amount of an enantiomer of Formula (I) or enantiomeric mixture wherein one enantiomer of Formula (I) predominates:

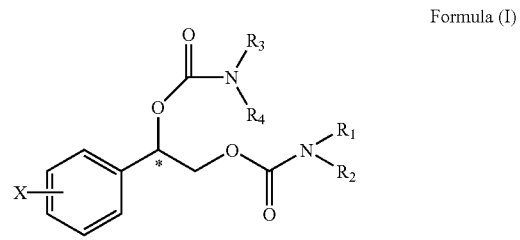

Formula (I)

wherein
phenyl is substituted at X with one to five halogen atoms selected from the group consisting of fluorine, chlorine, bromine and iodine; and,
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

Embodiments of the invention include a method for preventing or treating bipolar disorder comprising administering to a subject in need thereof a therapeutically effective amount of a pharmaceutical composition comprising a pharmaceutically acceptable carrier and an enantiomer of Formula (I) or enantiomeric mixture wherein one enantiomer of Formula (I) predominates.

Embodiments of the method include the use of an enantiomer of Formula (I) or enantiomeric mixture wherein one enantiomer of Formula (I) predominates for the preparation of a medicament for preventing or treating bipolar disorder in a subject in need thereof.

Embodiments of the method include the use of an enantiomeric mixture wherein one enantiomer of Formula (I) predominates to the extent of about 90% or greater. Embodiments of the method also include the use of an enantiomeric mixture wherein one enantiomer of Formula (I) predominates to the extent of about 98% or greater.

DETAILED DESCRIPTION OF THE INVENTION

The present invention is directed to a method for preventing or treating bipolar disorder comprising administering to a subject in need thereof a therapeutically effective amount of an enantiomer of Formula (I) or enantiomeric mixture wherein one enantiomer of Formula (I) predominates:

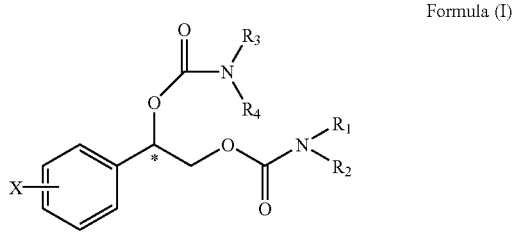

Formula (I)

wherein
phenyl is substituted at X with one to five halogen atoms selected from the group consisting of fluorine, chlorine, bromine and iodine; and,
$R_1$, $R_2$, $R_3$, and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

An embodiment of the invention includes a method for slowing or delaying the progression of bipolar disorder comprising administering to a subject in need thereof a therapeutically effective amount of an enantiomer of Formula (I) or enantiomeric mixture wherein one enantiomer of Formula (I) predominates.

The present method includes the use of an enantiomer of Formula (I) or enantiomeric mixture wherein one enantiomer of Formula (I) predominates wherein X is chlorine; preferably, X is substituted at the ortho position of the phenyl ring.

The present method also includes the use of an enantiomer of Formula (I) or enantiomeric mixture wherein one enantiomer of Formula (I) predominates wherein $R_1$, $R_2$, $R_3$ and $R_4$ are preferably selected from hydrogen.

For enantiomeric mixtures wherein one enantiomer of Formula (I) predominates, preferably, an enantiomer of Formula (I) predominates to the extent of about 90% or greater. More preferably, an enantiomer of Formula (I) predominates to the extent of about 98% or greater.

An embodiment of the present method includes the use of an enantiomer of Formula (Ia) or enantiomeric mixture wherein one enantiomer of Formula (Ia) predominates:

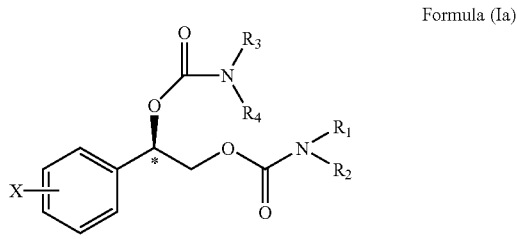

Formula (Ia)

wherein
phenyl is substituted at X with one to five halogen atoms selected from the group consisting of fluorine, chlorine, bromine and iodine; and,
$R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of an enantiomer of Formula (Ia) or enantiomeric mixture wherein one enantiomer of Formula (Ia) predominates wherein X is chlorine; preferably, X is substituted at the ortho position of the phenyl ring.

The present method also includes the use of an enantiomer of Formula (Ia) or enantiomeric mixture wherein one enantiomer of Formula (Ia) predominates wherein $R_1$, $R_2$, $R_3$ and $R_4$ are preferably selected from hydrogen.

For enantiomeric mixtures wherein one enantiomer of Formula (Ia) predominates, preferably, an enantiomer of Formula (Ia) predominates to the extent of about 90% or greater. More preferably, an enantiomer of Formula (Ia) predominates to the extent of about 98% or greater.

An embodiment of the present method includes a method for preventing or treating bipolar disorder comprising administering to a subject in need thereof a therapeutically effective amount of an enantiomer of Formula (Ib) or enantiomeric mixture wherein one enantiomer of Formula (Ib) predominates:

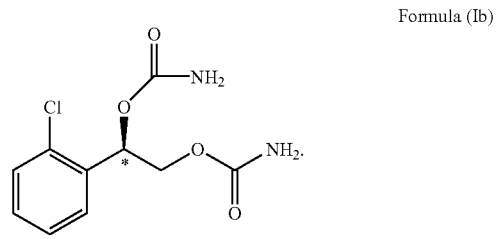

Formula (Ib)

For enantiomeric mixtures wherein one enantiomer of Formula (Ib) predominates, preferably, an enantiomer of Formula (Ib) predominates to the extent of about 90% or greater. More preferably, an enantiomer of Formula (Ib) predominates to the extent of about 98% or greater.

An embodiment of the invention includes a method for slowing or delaying the progression of bipolar disorder comprising administering to a subject in need thereof a therapeutically effective amount of an enantiomer of Formula (Ib).

Other crystal forms of compounds used in the present invention may exist and as such are intended to be included in the present invention.

It is apparent to those skilled in the art that the compounds of the invention are present as enantiomers and enantiomeric mixtures thereof. A carbamate enantiomer selected from the group consisting of Formula (I), Formula (Ia) and Formula (Ib) contains an asymmetric chiral carbon atom at the benzylic position, which is the aliphatic carbon adjacent to the phenyl ring (represented by the asterisk in the structural formulae).

Compounds of the present invention may be prepared as described in the previously referenced Bossinger '728 patent (incorporated by reference), Bossinger '692 patent (incorporated by reference) and Choi '759 patent (incorporated by reference).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The present invention contemplates a method for preventing or treating bipolar disorder in a subject in need thereof. Bipolar disorder includes, and is not limited to, bipolar disorder type I, bipolar disorder type II, cyclothymic disorder, rapid cycling, ultradian cycling, bipolar depression, acute mania, mania, mixed mania, hypomania or episodes associated with bipolar disorder.

An example of the method of the present invention comprises administering to the subject a therapeutically effective amount of an enantiomer of Formula (I) or enantiomeric mixture wherein one enantiomer of Formula (I) predominates in a pharmaceutical composition comprising a pharmaceutically acceptable carrier and an enantiomer of Formula (I) or enantiomeric mixture wherein one enantiomer of Formula (I) predominates. The method of the present invention also includes the use of an enantiomer of Formula (I) or enantiomeric mixture wherein one enantiomer of Formula (I) predominates for the preparation of a medicament for preventing or treating bipolar disorder.

Another example of the method of the present invention comprises administering to the subject a therapeutically effective amount of an enantiomer of Formula (I) or enantiomeric mixture wherein one enantiomer of Formula (I) predominates or a pharmaceutical composition thereof in combination with one or more agents useful in preventing or treating bipolar disorder.

An enantiomer of Formula (I) or enantiomeric mixture wherein one enantiomer of Formula (I) predominates or pharmaceutical composition thereof may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The therapeutically effective amount of an enantiomer of Formula (I) or enantiomeric mixture wherein one enantiomer of Formula (I) predominates or pharmaceutical composition thereof may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

The dosages, however, may be varied depending upon the requirement of the subjects (including factors associated with the particular subject being treated, including subject age, weight and diet, strength of the preparation, the advancement of the disease condition and the mode and time of administration) and the use of a particular enantiomer of Formula (I) or enantiomeric mixture wherein one enantiomer of Formula (I) predominates or pharmaceutical composition thereof.

Optimal dosages to be administered may be readily determined by those skilled in the art and will result in the need to adjust the dose to an appropriate therapeutic level. The use of either daily administration or post-periodic dosing may be employed. Preferably, an enantiomer of Formula (I) or enantiomeric mixture wherein one enantiomer of Formula (I) predominates or pharmaceutical composition thereof for preventing or treating bipolar disorder is administered orally or parenterally.

In accordance with the methods of the present invention, an enantiomer of Formula (I) or enantiomeric mixture wherein one enantiomer of Formula (I) predominates or pharmaceutical composition thereof described herein may be administered separately, at different times during the course of therapy or concurrently in divided combination or single combination forms. Advantageously, an enantiomer of Formula (I) or enantiomeric mixture wherein one enantiomer of Formula (I) predominates or pharmaceutical composition thereof may be administered in a single daily dose or the total daily dosage may be administered via continuous delivery or in divided doses of two, three or four times daily. The instant invention is therefore to be understood as embracing all such methods and regimes of simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare a pharmaceutical composition of the present invention, an enantiomer of Formula (I) or enantiomeric mixture wherein one enantiomer of Formula (I) predominates as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as

*Pharmaceutical Dosage Forms: Tablets, Second Edition, Revised and Expanded*, Volumes 1–3, edited by Lieberman et al; *Pharmaceutical Dosage Forms: Parenteral Medications*, Volumes 1–2, edited by Avis et al; and *Pharmaceutical Dosage Forms: Disperse Systems*, Volumes 1–2, edited by Lieberman et al; published by Marcel Dekker, Inc.

Preferably, a pharmaceutical composition is in a unit dosage form such as a tablet, pill, capsule, caplet, gelcap, lozenge, granule, powder, sterile parenteral solution or suspension, metered aerosol or liquid spray, drop, ampoule, autoinjector device or suppository for administration by oral, intranasal, sublingual, intraocular, transdermal, parenteral, rectal, vaginal, inhalation or insufflation means. Alternatively, the composition may be presented in a form suitable for once-weekly or once-monthly administration or may be adapted to provide a preparation for intramuscular injection.

In preparing a pharmaceutical composition having a solid dosage form for oral administration, such as a tablet, pill, capsule, caplet, gelcap, lozenge, granule or powder (each including immediate release, timed release and sustained release formulations), suitable carriers and additives include but are not limited to diluents, granulating agents, lubricants, binders, glidants, disintegrating agents and the like. If desired, tablets may be sugar coated, gelatin coated, film coated or enteric coated by standard techniques.

For preparing a solid dosage form, the principal active ingredient is mixed with a pharmaceutical carrier (e.g. conventional tableting ingredients such as diluents, binders, adhesives, disintegrants, lubricants, antiadherents and glidants). Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

In preparing a pharmaceutical composition having a liquid dosage form for oral, topical and parenteral administration, any of the usual pharmaceutical media or excipients may be employed. Thus, for liquid unit dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form. The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

BIOLOGICAL EXPERIMENTAL EXAMPLES

The activity of an enantiomer of Formula (I) (or an enantiomeric mixture wherein one enantiomer of Formula (I) predominates) for use in preventing or treating bipolar disorder was evaluated in the following experimental examples which are intended to be a way of illustrating but not limiting the invention.

Hippocampal Kindled Rat Model

In the hippocampal kindling model (Lothman E W, et al., *Epilepsy Res.*, 1988, 2(6) 367–79), adult male Sprague-Dawley rats are surgically implanted with bipolar electrodes. Seizure score is assessed as follows: (1) mouth and facial movements; (2) above symptoms plus head nodding; (3) above symptoms plus forelimb clonus; (4) above symptoms plus rearing; and (5) above symptoms plus falling.

Results for Hippocampal Kindled Rat Model

Example 1

An enantiomer of Formula (Ib) was administered intraperitoneally and was found to be effective against the expression of Stage 5 seizures at a nontoxic dose of 300 mg/kg in hippocampal kindled rats (n=2) over a 4 hour time period.

As shown in Table 1, the effect for the enantiomer of Formula (Ib) on the expression of Stage 5 seizures in the hippocampal-kindled rat model was dose-dependent.

TABLE 1

| Time (hr) | Mean Seizure Score | After-Discharge Threshold (mA) | After-Discharge Duration (sec) |
|---|---|---|---|
| Control | 5 | 95 | 68 |
| 0.25 | 2.5 | 105 | 44 |
| 1 | 1.5 | >200 | 50 |
| 2 | 1.5 | >200 | 53 |
| 4 | 2.5 | 200 | 111 |

Example 2

An enantiomer of Formula (Ib) was administered intraperitoneally and was found to have a time-dependent reduction in after-discharge threshold and duration at a nontoxic dose of 50 mg/kg in hippocampal kindled rats (n=8 for each group tested) over approximately a 3 hour time period.

As shown in Table 2, the results were statistically significant ($p<0.05$) from predose control for the amount of rats protected in each group (% protection), the average reduction in seizure scores for the total number of animals at each dose level (mean seizure score) and in after-discharge duration. Over a dose range from 50 to 200 mg/kg, the calculated $ED_{50}$ value for reduction of the seizure score from 5 to 3 or less was 112 mg/kg with a 95% confidence interval of 67.9 to 189.8 mg/kg.

TABLE 2

| Dose (mg/kg) | n | % Protected | Mean Seizure Score | After-Discharge Duration (sec) |
|---|---|---|---|---|
| 50 | 8 | 12.50% | 3.75 | 75.88 |
| 100 | 8 | 33.33% | 3 | 53.17 |
| 200 | 8 | 87.50% | 1.63 | 42 |

An enantiomer of Formula (Ib) has potent anti-kindling effects in the hippocampal-kindled rat model.

While the foregoing specification teaches the principles of the present invention, with examples provided for the purposes of illustration, it will be understood that the practice of the invention encompasses all of the usual variations, adaptations and/or modifications as come within the scope of the following claims and their equivalents.

What is claimed is:

1. A method for treating bipolar disorder comprising administering to a subject in need thereof a therapeutically effective amount of an enantiomer of Formula (I) or enantiomeric mixture wherein one enantiomer of Formula (I) predominates:

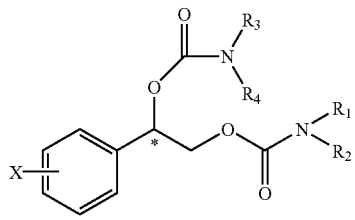

Formula (I)

wherein
  phenyl is substituted at X with one to five halogen atoms selected from the group consisting of fluorine, chlorine, bromine and iodine; and,
  $R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

2. The method of claim 1 wherein X is chlorine.

3. The method of claim 1 wherein X is substituted at the ortho position of the phenyl ring.

4. The method of claim 1 wherein $R_1$, $R_2$, $R_3$ and $R_4$ are selected from hydrogen.

5. The method of claim 1 wherein the enantiomer of Formula (I) is an enantiomer of Formula (Ia):

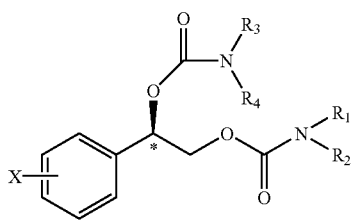

Formula (Ia)

wherein
  phenyl is substituted at X with one to five halogen atoms selected from the group consisting of fluorine, chlorine, bromine and iodine; and,
  $R_1$, $R_2$, $R_3$ and $R_4$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

6. The method of claim 5 wherein X is chlorine.

7. The method of claim 5 wherein X is substituted at the ortho position of the phenyl ring.

8. The method of claim 5 wherein $R_1$, $R_2$, $R_3$ and $R_4$ are selected from hydrogen.

9. The method of claim 5 wherein the enantiomer of Formula (Ia) predominates to the extent of about 90% or greater.

10. The method of claim 5 wherein the enantiomer of Formula (Ia) predominates to the extent of about 98% or greater.

11. The method of claim 1 wherein the enantiomer of Formula (I) is an enantiomer of Formula (Ib):

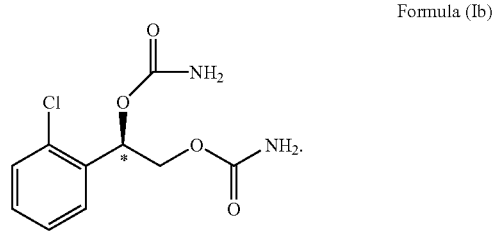

Formula (Ib)

12. The method of claim 11 wherein the enantiomer of Formula (Ib) predominates to the extent of about 90% or greater.

13. The method of claim 11 wherein the enantiomer of Formula (Ib) predominates to the extent of about 98% or greater.

14. The method of claim 1 wherein bipolar disorder is selected from the group consisting of bipolar disorder type I, bipolar disorder type II cyclothymic disorder, rapid cycling, ultradian cycling, bipolar depression, acute mania, mania, mixed mania, hypomania and episodes associated with bipolar disorder.

15. The method of claim 1 wherein the therapeutically effective amount is from about 0.01 mg/Kg/dose to about 100 mg/Kg/dose.

16. The method of claim 1 wherein the method is a method for slowing or delaying the progression of bipolar disorder comprising administering to a subject in need thereof a therapeutically effective amount of an enantiomer of Formula (I) or enantiomeric mixture wherein one enantiomer of Formula (I) predominates.

17. The method of claim 16 wherein the therapeutically effective amount is from about 0.01 mg/Kg/dose to about 100 mg/Kg/dose.

* * * * *